(12) United States Patent
Grafinger

(10) Patent No.: US 6,488,711 B1
(45) Date of Patent: Dec. 3, 2002

(54) KNEE-JOINT PROSTHESIS

(76) Inventor: Josef Grafinger, Ottakringerstrasse 215/4/2/7, D-1160 Vienna (AT)

(*) Notice: Subject to any disclaimer, the term of this patent is extended or adjusted under 35 U.S.C. 154(b) by 0 days.

(21) Appl. No.: 09/555,111
(22) PCT Filed: Dec. 18, 1998
(86) PCT No.: PCT/AT98/00315
§ 371 (c)(1),
(2), (4) Date: May 24, 2000
(87) PCT Pub. No.: WO99/32052
PCT Pub. Date: Jul. 1, 1999

(30) Foreign Application Priority Data

Dec. 19, 1997 (AT) .............................. 2150/97

(51) Int. Cl.$^7$ .................................................. A61F 2/38
(52) U.S. Cl. .................................. 623/20.24; 623/20.27
(58) Field of Search ........................... 623/18.11, 19.12, 623/20.14, 20.22, 20.27, 21.11–21.17, FOR 21, 20.24

(56) References Cited

U.S. PATENT DOCUMENTS 3,837,008 A * 9/1974 Bahler et al. ............ 623/21.13
4,655,201 A * 4/1987 Pirmantgen .............. 623/39 X

FOREIGN PATENT DOCUMENTS

JP        5-168656        *  7/1993

* cited by examiner

Primary Examiner—Bruce Snow
Assistant Examiner—Brian E. Pellegrino
(74) Attorney, Agent, or Firm—Herbert Dubno; Andrew Wilford

(57) ABSTRACT

The invention relates to a (knee) joint for positioning two pivoting parts in such a way that they can pivot within a limited range. According to the invention, a combined turning and sliding movement is produced by means of curved guides (6, 6', 7, 7'). A cam body (8) connected to one pivoting part, e.g. the lower leg, has two cams (10, 11; 13, 14), preferably on each side. Said cams interact with the curved guides (6, 6', 7, 7'). The curved guides (6, 6', 7, 7') are located in half-shells (3, 4) which are connected to the second pivoting part, e.g. the upper leg. Parts of the inventive knee joint which are subject to wear are relatively easy to replace and movement sequences can also be modified when replacements are made.

6 Claims, 5 Drawing Sheets

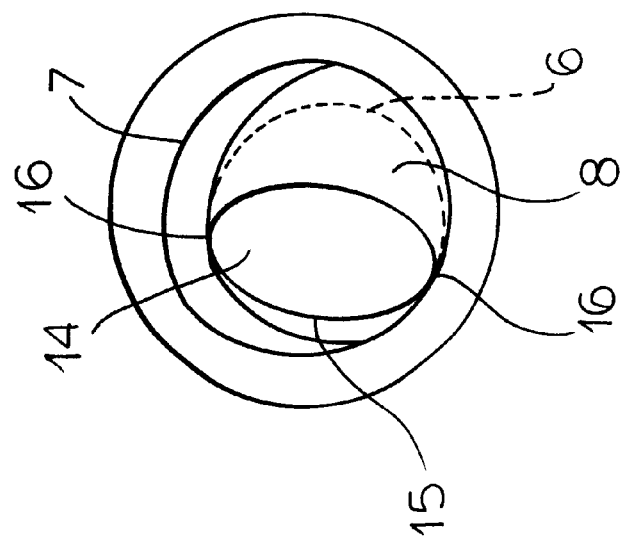
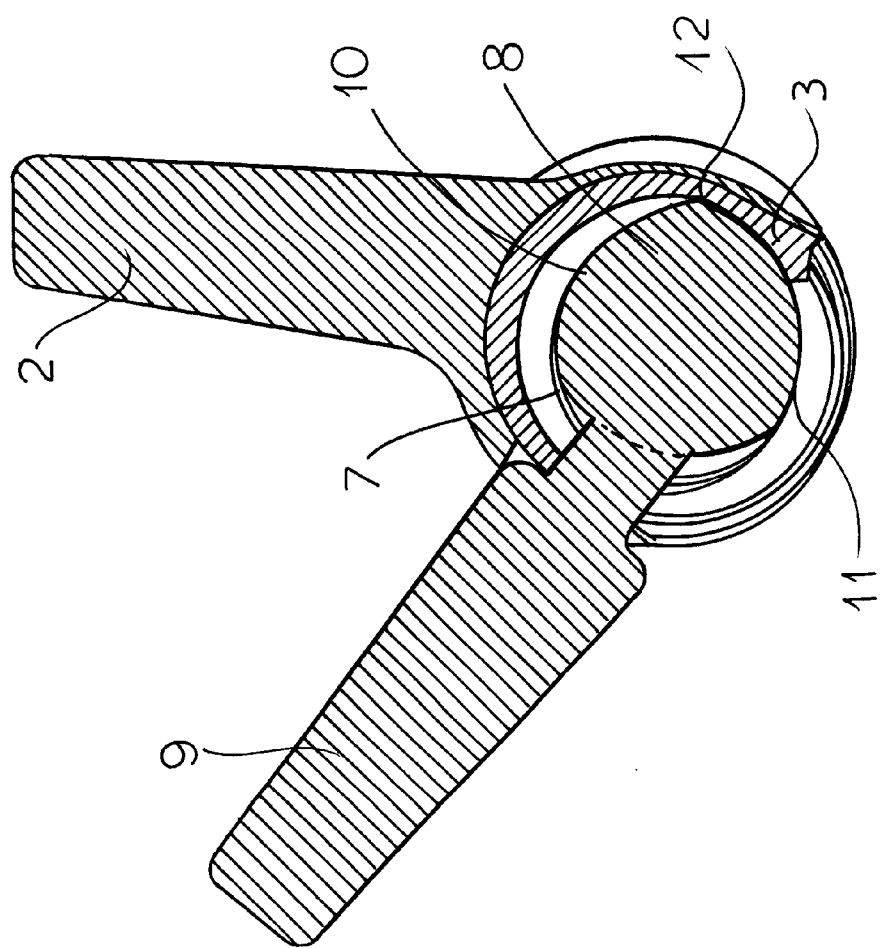
FIG. 4A
FIG. 4

KNEE-JOINT PROSTHESIS

This application is the US national phase of PCT application PCT/AT98/00315 filed Dec. 18, 1998 with a claim to the priority of Austrian application A2150/97 filed Dec. 19, 1997.

FIELD OF THE INVENTION

The invention relates to a joint (knee joint) for limited relative pivoting of two parts, in particular human body parts, where arcuate guides produce a combined pivoting and sliding.

BACKGROUND OF THE INVENTION

The problem in making various joints, in particular knee joints, is mainly in reproducing the natural movement of the joint, which natural movement is not a simple pivoting but a combined pivoting and sliding.

Austrian 393,620 describes a joint for a knee brace where two arcuate guides formed in a first brace part are engaged by two pins limiting the pivot angle of the two brace parts. The pins or bolts thus form in every position the axis for the arcuate guiding of the other pins. The natural movement of the knee cannot be duplicated by such an arrangement.

U.S. Pat. No. 5,009,223 describes joints for knee braces where in addition to the two arcuate guides there are two further arcuate guides. These two additional guides form a sort of T, with one T-arm carrying a bolt and the other T-arm another bolt of another side rail. Even in this known arrangement it is not possible to guide in a natural movement.

OBJECT OF THE INVENTION

The object of the invention is to produce a joint of the above-mentioned types that produces a combined pivoting and sliding movement and that is usable in particular but not exclusively as a replacement for a human knee joint. It should also be possible to relatively easily replace wear-prone parts and even produce by changing parts a different movement pattern.

SUMMARY OF THE INVENTION

This is attained in that a cam body on one of the pivotal parts, e.g. the tibia, preferably has two sides each with two cams that coact with respective arcuate guides that are formed in cups that are connected with the second pivotal part, e.g. the femur.

Such an arrangement produces a combined pivotal and slide movement that be adjusted by changing the shape of the arcuate guides for different requirements. Replacement of the wear parts is also relatively simple.

According to a preferred embodiment of the invention, the cam body has two cylindrical surfaces forming a cam and meeting at a rounded edge and two projections extending perpendicular to the pivot direction and forming second cams and the guides are offset in two steps in the cups. With this it is preferable when the cam body is shaped in section as a triangle with rounded corners.

The projecting second cams are formed on the side of the rounded triangle opposite the point of the two cylindrical surfaces. The connection of one of the pivotal parts is arranged opposite the point of the two cylindrical surfaces.

In order to hold the two cups these are partially surrounded by a holder on which the connection for the other pivotal part is arranged. The cups are fitted to the holder so that they can be switched easily.

BRIEF DESCRIPTION OF THE DRAWING

In the following the invention is more closely described with reference to an embodiment shown in the drawings, without being limited to this embodiment. Therein:

FIG. 4 is a longitudinal section through the joint in a maximally flexed position;

FIG. 4A illustrates the main guide parts of the joint in the position of FIG. 4.

SPECIFIC DESCRIPTION

Figure 1:
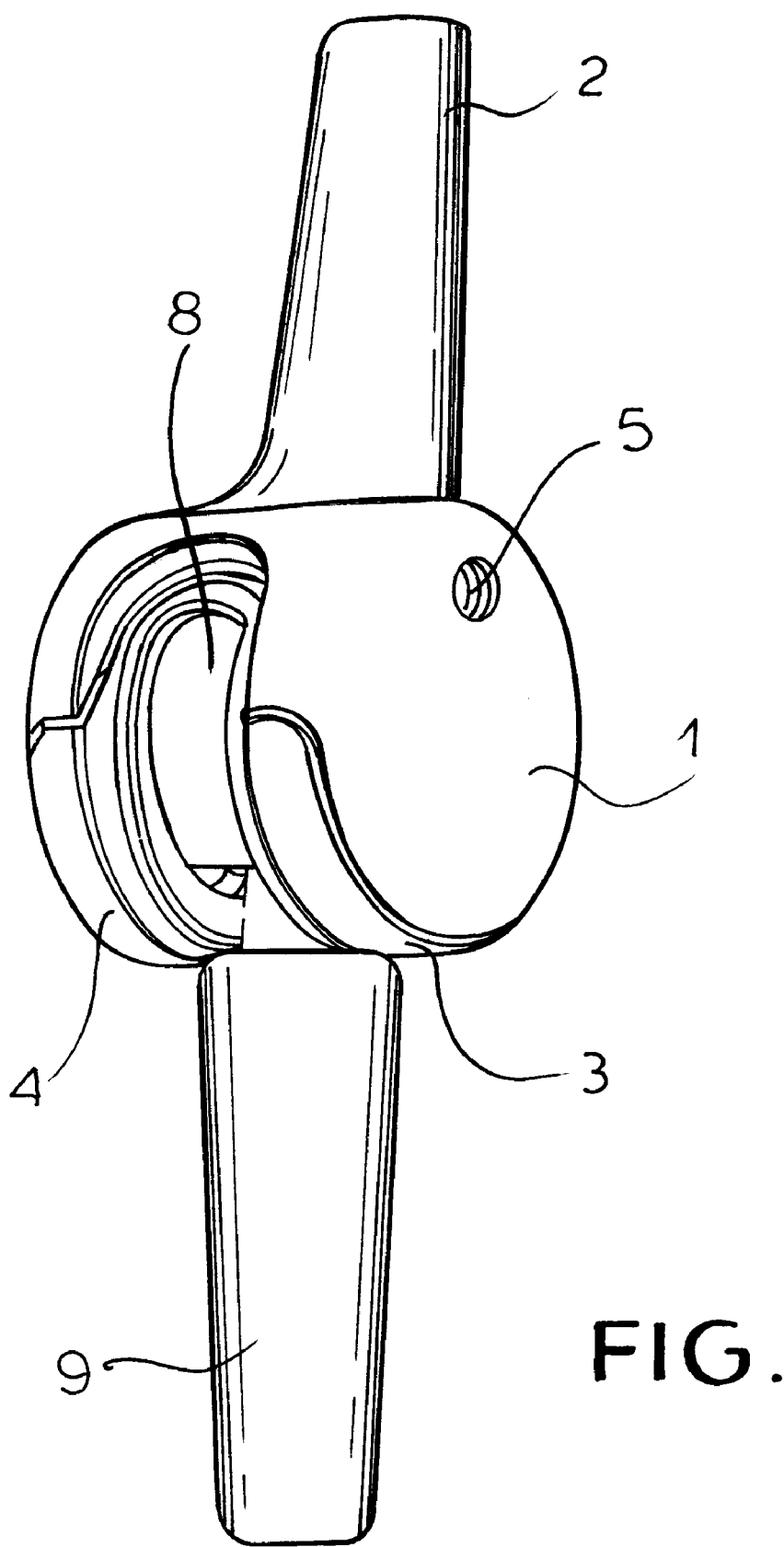
FIG. 1 is a perspective view of a joint according to the invention.
Figure 2:
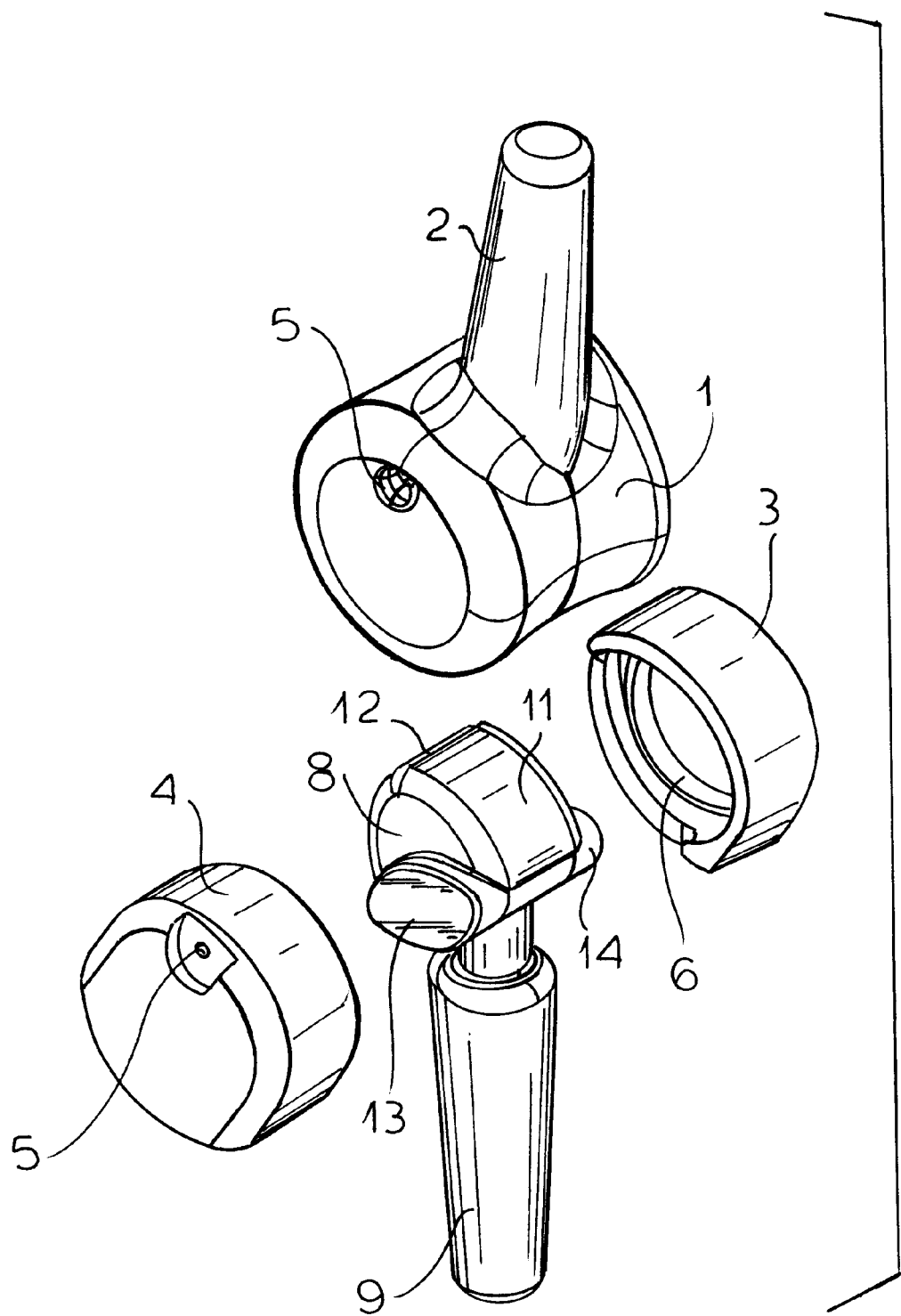
FIG. 2 is an exploded view of the joint of FIG. 1.

The embodiment according to the drawing is a knee prosthesis. Therein a holder 1 carries a connection pin 2 that is connected with the femur. The holder 1 is fitted with two cups 3 and 4 that are secured on the holder 1 via bores 5 formed partly in the cups 3 and 4 and partly in the holder 1 and by unillustrated screws. The cups 3 and 4 form arcuate outer guides 6 and 6' and arcuate center or inner guides 7 and 7', the guides 7 and 7' being offset in steps from the respective guides 6 and 6' along an axis perpendicular to the view plane of FIGS. 3 and 4.

The cups 3 and 4 hold a cam body 8 on which a pin 9 is provided that is fitted into the tibia. The cam body 8 is of generally rounded triangular section. Two cylinder surfaces 10 and 11 meet at a rounded edge 12 that is opposite the pin 9. These two cylindrical surfaces 10 and 11 form a center cam of the cam body 8, riding on the arcuate inner or center guides 7 and 7'.

Outer cams 13 and 14 that coact with the arcuate outer guides 6 and 6' project axially from the sides of the cam body 8. These cams 13 and 14 have in the illustrated embodiment an elliptical section, with one part 15 of larger radius of curvature also forming the third side of the body 8 and the two parts 16 of smaller radius of curvature riding on the arcuate guides 6 and 6'.

Figure 3A:
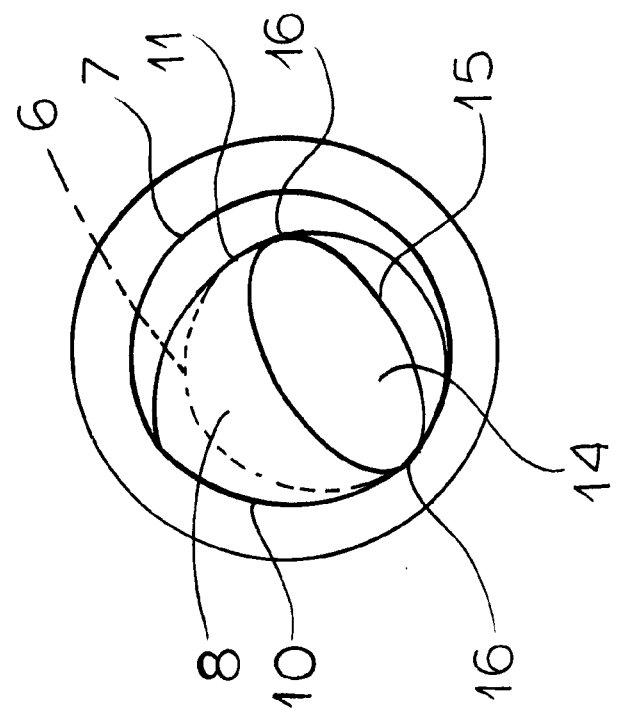
FIG. 3A illustrates the main guide parts of the joint in the position of FIG. 3.
Figure 3:
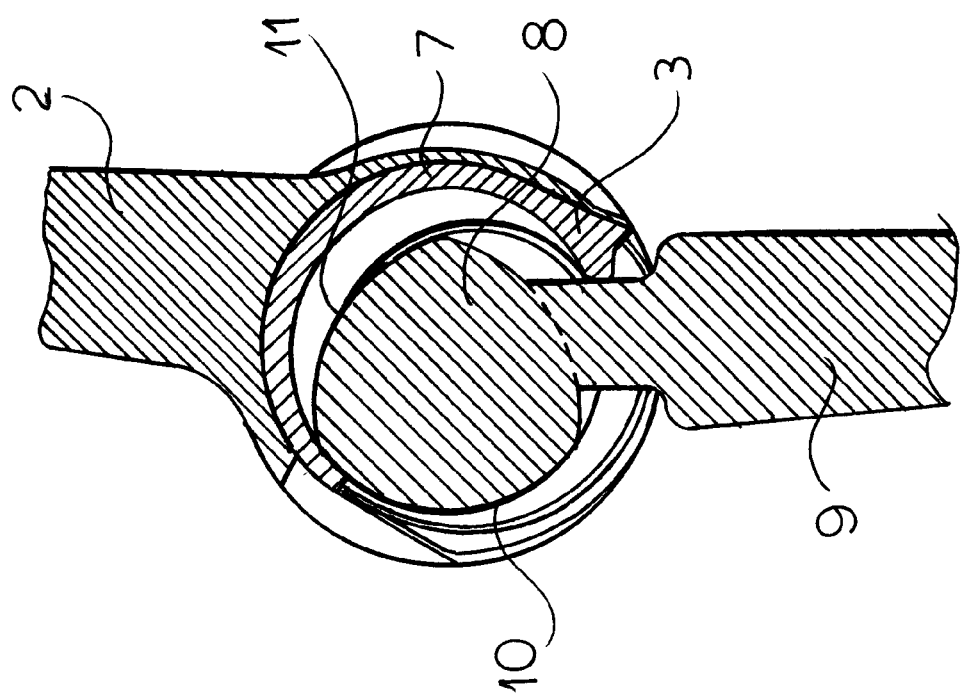
FIG. 3 is a longitudinal section through the joint in an extended position.
Figure 5:
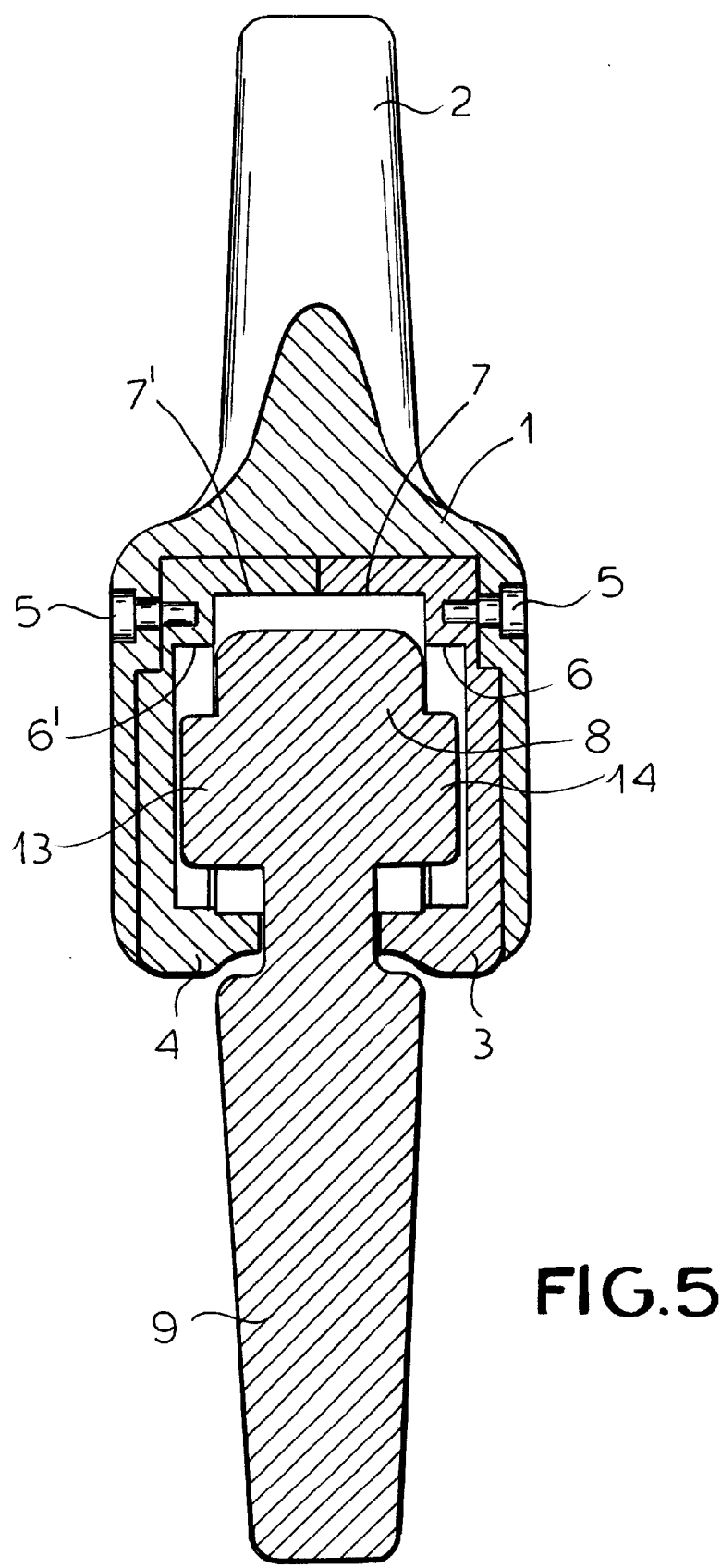
FIG. 5 is a section through the joint along a section plane perpendicular to the plane of the view of FIG. 3.

As visible in FIGS. 3 and 3A, in an extended position of the joint the cylindrical surface 10 engages the guides 7 and 7' and the cylindrical surface 11 engages nothing. In the extended the pin 9 engages the cups 3 and 4. In order to ensure exact positioning, mechanical abutment of the pin 9 on the cups 3 and 4 is about 1° ahead of mechanical abutment of the cylindrical surface 10 on the guide 7, 7'.

In the most flexed position according to FIGS. 4 and 4A, the pin 9 engages the opposite outer edges of the cups 3 and 4. In this position the cylindrical surface 10 is out of contact with the guide 7, 7' and the cylindrical surface 11 is riding on the guide 7, 7'. Even here it is preferable when mechanical abutment between the pin 9 and the cups 3 and 4 is about 1° ahead of mechanical abutment between the cylindrical surface 11 and the guide 7.

Numerous variations are possible within the scope of the invention. Thus a joint according to the invention can as a result of the free formation of the control surfaces also be used for other body joints and prosthesis. If a combined pivoting and sliding movement is required in other fields, the joint according to the invention can be used.

What is claimed is:

1. A prosthetic knee joint for installation between a pair of leg bones, the joint comprising:

a cam body for mounting on one of the bones and having a center cam having a pair of part-cylindrical surfaces meeting at a rounded corner, the cam body being formed with a pair of oppositely directed projections having outer surfaces each at least partially offset from the respective part-cylindrical surface and forming outer cams flanking and radially offset from the center cam; and a pair of guide cups for mounting on the other of the bones, receiving the cam body, and each formed internally with respective center and outer arcuate guides engageable in angularly differently offset positions of the bones with the respective cams, the cams and guides being shaped such that on pivoting of the cam body in the guide cups the cams slide on the respective guides.

2. The prosthetic knee joint defined in claim 1 wherein the cam body is of generally triangular section at the center cam.

3. The prosthetic knee joint defined in claim 1 wherein the projections are offset on the cam body away from the rounded corner.

4. The prosthetic knee joint defined in claim 1 wherein the cam body has a pin for connection to the one bone, the projections being offset oppositely on the cam body from the pin.

5. The prosthetic knee joint defined in claim 1, further comprising a holder provided with a pin for connection to the other bone, the guide cups being mounted on the holder.

6. The prosthetic knee joint defined in claim 5 wherein the guide cups are separable from the holder.

\* \* \* \* \*